US00PP13246P3

(12) United States Plant Patent
Utecht

(10) Patent No.: US PP13,246 P3
(45) Date of Patent: Nov. 19, 2002

(54) GERANIUM PLANT NAMED 'FISEYELY'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/991,634

(22) Filed: Nov. 26, 2001

(65) Prior Publication Data

US 2002/0038473 P1 Mar. 28, 2002

(51) Int. Cl.[7] ..... A01H 5/00

(52) U.S. Cl. ..... Plt./329
(58) Field of Search ..... Plt./329, 325

*Primary Examiner*—Kent L. Bell
(74) *Attorney, Agent, or Firm*—Foley & Lardner

(57) ABSTRACT

A new and distinct cultivar of geranium plant named 'Fiseyely', as described and illustrated, and particularly characterized by the combined features of deep lavender colored flowers with deep red markings, relatively large, semi-spherically shaped umbels well above the foliage, mid season spring flower response, large, medium green leaves with slight zonation, and medium to tall, well-branched and uniformly rounded plant habit.

1 Drawing Sheet

BOTANICAL CLASSIFICATION

*Pelargonium zonale.*

VARIETY DENOMINATION

'Fiseyely'.

BACKGROUND OF THE INVENTION

The present invention comprises a new and distinct cultivar of geranium, botanically known as *Pelargonium zonale*, and hereinafter referred to by the cultivar name 'Fiseyely'.

'Fiseyely' is a product of a planned breeding program which had the objective of creating new geranium varieties with violet or lavender flower color, medium green foliage, and medium sized plant habit.

'Fiseyely' originated from a hybridization made by the inventor Angelika Utecht in a controlled breeding program in Galdar, Gran Canaria, Spain, in 1996. The female parent was an unpatented hybrid seedling, no. K93-780-32, having lavender colored, single-type flowers, uniform, medium green foliage, and relatively compact plant habit. The male parent of 'Fiseyely' was the patented variety 'Fislypso' (U.S. Plant Pat. No. 11,162), which is characterized by violet flowers with white eyes, medium green foliage with weak zonation, and relatively low and compact plant habit with the umbels well above the foliage.

'Fiseyely' was selected as one flowering plant within the progeny of the stated cross by Angelika Utecht in 1997, in a controlled environment in Galdar, Gran Canaria, Spain. The first act of asexual reproduction of 'Fiseyely' was accomplished when vegetative cuttings were taken from the initial selection in the fall of 1997 in a controlled environment in Galdar, Gran Canaria, Spain, by, or under the supervision of, Angelika Utecht.

Horticultural examination of plants grown from cuttings of the plant initiated in May 1998 in Hillscheid, Federal Republic of Germany, and continuing thereafter, has demonstrated that the combination of characteristics as herein disclosed for 'Fiseyely' are firmly fixed and are retained through successive generations of asexual reproduction. The new cultivar reproduces true to type.

'Fiseyely' has not been observed under all possible environmental conditions. The phenotype may vary significantly with variations in environment such as temperature, light intensity and day length. The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fiseyely' in combination distinguish this geranium as a new and distinct cultivar:

1. deep lavender colored, semi-double flowers with purple-red or deep red markings;
2. medium to large, semi-spherically shaped inflorescence;
3. medium-green, relatively large foliage with weak zonation;
4. moderately vigorous growth, and medium to tall, uniform and rounded plant habit; and
5. mid season spring flowering response.

Of the many commercial cultivars known to the present inventor, the most similar in comparison to 'Fiseyely' are 'Fislypso' and the patented variety 'Fiseye' (U.S. Plant Pat. No. 11,302). In comparison to 'Fislypso', 'Fiseyely' has a similar main flower color, but red eyes on petals, which 'Fislypso' lack. Furthermore, 'Fiseyely' grows more vigorously and develops a taller, primarily higher, foliage canopy. Both flowers and inflorescences are somewhat larger, but peduncles are not quite as long as those of 'Fislypso', accordingly, umbels of 'Fiseyely' are borne at an ideal height above the foliage, while peduncles of 'Fislypso' may appear too long in relation to the relatively low plant habit.

In comparison to 'Fiseye', 'Fiseyely' has a deeper violet main flower color, its umbels are born higher above the foliage canopy, and foliage is weakly zoned, in contrast to the uniformly green leaves of 'Fiseye'.

BRIEF DESCRIPTION OF THE DRAWING

The accompanying photographic drawing shows typical flower and foliage characteristics of 'Fiseyely' with colors being as true as possible with an illustration of this type. The drawing shows a flowering pot plant in a 14 cm container.

DETAILED BOTANICAL DESCRIPTION

In the following description color references are made to The Royal Horticultural Society Colour Chart (R.H.S.). The color values were determined indoors from plants developed in a greenhouse in May 2001, in Hillscheid, Germany. The measurements were taken in Langley, British Columbia, Canada, in early July, 2001, 18 weeks after planting of rooted cuttings. The plants were growing in 8 inch containers, they had not been pinched.

Inflorescence:
- *Type.*—Umbel.
- *Shape.*—Semi-spherical.
- *Average diameter.*—128 mm.
- *Average depth.*—59 mm.
- *Peduncle length.*—176 mm.
- *Peduncle color.*—Light green, RHS 143 A to 144 A.
- *Pedicel length.*—29 mm.
- *Pedicel color.*—Lower part light green, RHS 144 B, upper part reddish-brown, RHS 184 A.
- *Number of flowers per umbel.*—About 30.

Corolla:
- *Average diameter.*—50.2 mm.
- *Form.*—Semi-double.
- *Shape.*—Mainly round, weakly cup-shaped.
- *Number of petals.*—8.2.
- *Petaloids.*—When present, Irregular in shape and color is between RHS 78 B to light violet, near RHS 75 D (particularly near base) (Both surfaces).
- *Shape of petals.*—Obovate, base attenuate, upper end is rounded, margins are somewhat wavy, mainly entire, but may be slightly serrulated at the tips.
- *Size of petals.*—Upper petals length 28–30 mm, width: 20–24 mm; lower petals length 25–27 mm, width: 24–26 mm.
- *Color (general tonality from a distance of three meters)* .—Deep lavender.
- *Color of upper petals.*—Main part RHS 78 B.
- *Markings of upper petals.*—Small to medium sized macules, RHS 66 B, and small white base, RHS 155 D, and veins, RHS 74 B.
- *Color of lower petals.*—RHS 78 B.
- *Markings of lower petals.*—Very small dark pink macules, RHS 74 C.
- *Color of lower surface of petals.*—RHS 75 A to RHS 75 D, most intense near margin, almost white at center, and pink veins RHS 74 D.
- *Color of sepals.*—Outer surface: mainly light green, RHS 144 A, weak, brown RHS 179 A at the base; inner surface light green, RHS 144 A to RHS 144 B.
- *Number of sepals.*—Approximately 6.
- *Shape of sepals.*—Linear to lanceolate, acute tip, truncate base, surface with moderate pubescence, margin entire.
- *Size of sepals.*—12 mm long, 4 mm wide for the largest upper sepal, 2–3 mm in width for the other sepals.

Bud: (just before petals unfold):
- *Shape.*—Narrow elliptic to elliptic.
- *Color (sepals).*—Light green, RHS 144 A.
- *Color (petals).*—Purple-pink, marbled, RHS 73 A and 73 D.
- *Length.*—19 mm.
- *Width.*—9 mm.

Reproductive organs:
- *Androecium.*—About 5 fertile anthers, filaments mainly white, RHS 155 D, to very light pink near the tips, RHS 68 B; moderate pollen, orange, RHS 30 A.
- *Gynoecium.*—One pistil, style and stigma dark-red, RHS 53 C, 5 to 6 lobed stigma.
- *Fertility/seed set.*—Occasionally a few seeds are developed. Fruit: Oblong, about 6 mm in diameter, with rostrum (beak), total length about 42 mm. Seed: Oblong, 4–5 mm long, brown, RHS 177 B.

Spring flowering response period: In Hillscheid, Germany, in 2000, plants had on average 0.9 flowers opened 8 weeks after planting of rooted cuttings.

Outdoor flower production: Continuously flowering, moderately rich flowering, the flower count in 2000, in Hillscheid, Germany, indicated about 2.2 inflorescences per plant in mid May.

Durability: Good stability of flower color, relatively good rain resistance.

Lastingness of the individual flower: About 7–8 days at 18° C., about 16–18 days for the umbel.

Pest/disease resistance/susceptibility: No observations made.

Fragrance: None.

PLANT

Foliage:
- *Shape.*—Kidney-shaped, with cordate base, weak to medium lobes, at the base open.
- *Margin.*—Bicrenated.
- *Texture.*—Upper surface smooth, velvety.
- *Size of leaf.*—103 mm wide, 63 mm long.
- *Color of upper surface.*—Medium green, approximately RHS 137 B to 137 C.
- *Color of zonation.*—Brownish green, about RHS 147 A, relatively weak.
- *Color of lower surface.*—RHS 137 D.
- *Petioles.*—50–60 mm long, 3 mm in diameter, light green in color, approximately RHS 143 A.

General appearance and form:
- *Stem color.*—Green, RHS 144 A to RHS 144 B.
- *Internode length.*—10–20 mm.
- *Branching pattern.*—Average 7.4 branches.
- *Size of plants.*—Height 27.4 cm, width 49.2 cm, as measured from the top of the soil (base of the main stem) to the surface of the foliage canopy, without inflorescences.

I claim:

1. A new and distinct cultivar of geranium plant named 'Fiseyely', as described and illustrated herein.

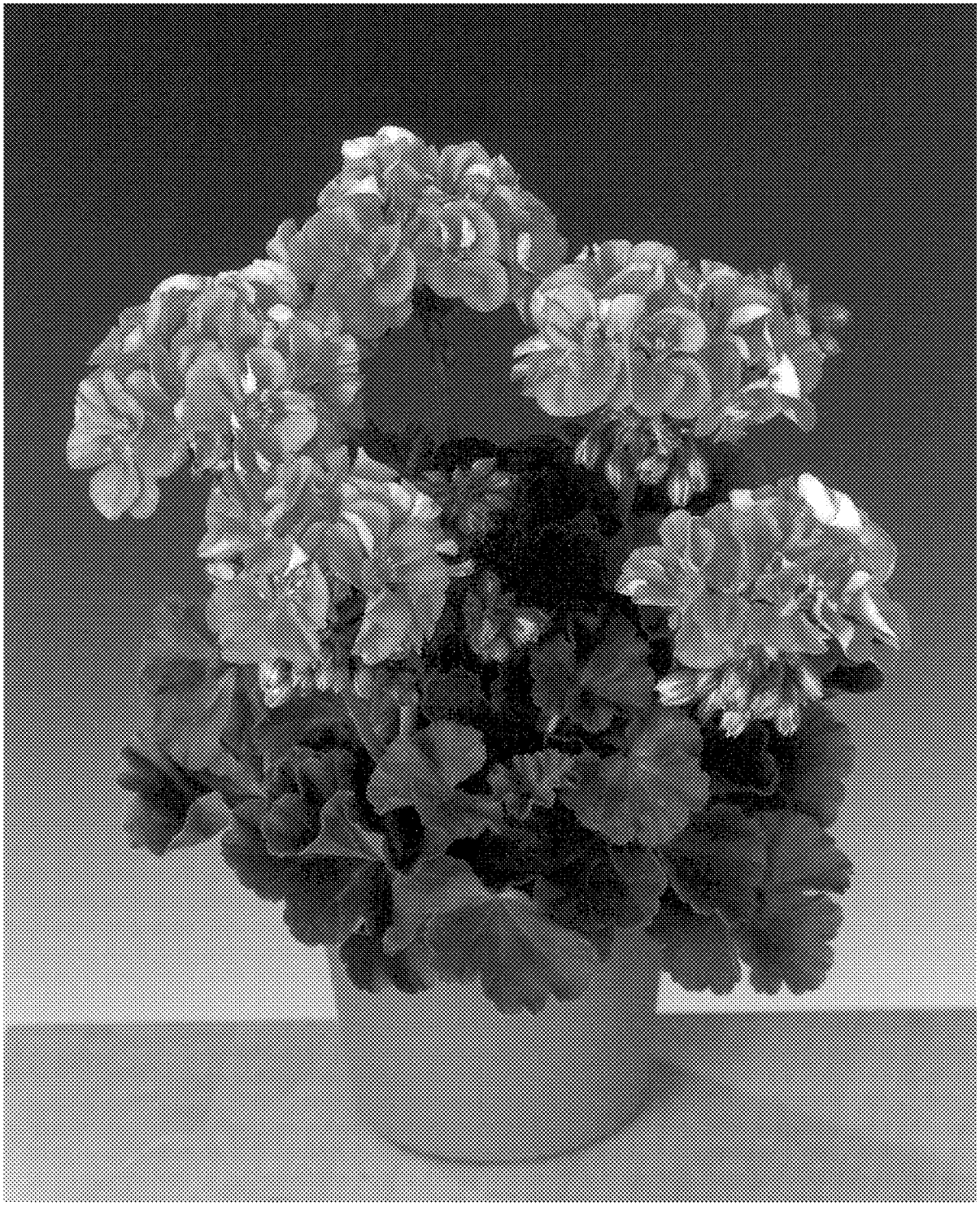

* * * * *